United States Patent [19]

Shoshi

[11] Patent Number: 5,227,512
[45] Date of Patent: Jul. 13, 1993

[54] STILBENE COMPOUND, INTERMEDIATE FOR PRODUCING THE STILBENE COMPOUND, METHOD OF PRODUCING THE STILBENE COMPOUND, AND LIQUID CRYSTAL COMPOSITION CONTAINING THE STILBENE COMPOUND

[75] Inventor: Masayuki Shoshi, Yokohama, Japan

[73] Assignee: Ricoh Company, Ltd., Tokyo, Japan

[21] Appl. No.: 630,888

[22] Filed: Dec. 20, 1990

[30] Foreign Application Priority Data

Dec. 20, 1989 [JP] Japan .................................. 1-330241

[51] Int. Cl.[5] ............................................ C07C 69/76
[52] U.S. Cl. ........................................ 560/64; 560/53
[58] Field of Search ........................................ 560/64

[56] References Cited

PUBLICATIONS

CA 97(17):144507w 1982.

Primary Examiner—Paul J. Killos
Attorney, Agent, or Firm—Oblon, Spivak, McClelland, Maier & Neustadt

[57] ABSTRACT

An optically active stilbene compound of formula (I):

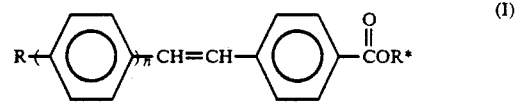

wherein R is an alkoxy group with 20 or less carbon atoms; n is an integer of 1 or 2; and R* is an optically active group, a substituted benzylphosphonate compound of formula (II) serving as an intermediate for preparing the above active stilbene compound,

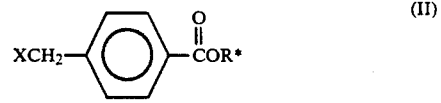

wherein X represents

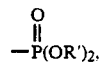

R' is an alkyl group having 1 to 5 carbon atoms, or an unsubstituted or substituted aryl group; and R* is the same as in formula (I), a method of producing the optically active stilbene compound of formula (I), and a liquid crystal composition containing the optically active stilbene compound of formula (I) are disclosed.

2 Claims, 3 Drawing Sheets

STILBENE COMPOUND, INTERMEDIATE FOR PRODUCING THE STILBENE COMPOUND, METHOD OF PRODUCING THE STILBENE COMPOUND, AND LIQUID CRYSTAL COMPOSITION CONTAINING THE STILBENE COMPOUND

BACKGROUND OF THE INVENTION

1. Field of the Invention

The present invention relates to an optically active stilbene compound used as a liquid crystal material; to an intermediate for, and to a method for producing the optically active stilbene compound; and to a liquid crystal composition containing the optically active stilbene compound.

2. Discussion of Background

At the present time, liquid crystal materials are widely used as display elements. Almost all these liquid crystal display elements, however, are the TN (Twisted Nematic) type of display systems which utilize nematic liquid crystals. This type of liquid crystal display element has the drawback that its response speed is low, inasmuch as the response speeds obtained are in the order of several seconds, at the best.

For this reason, various types of liquid crystal display systems based on other principles have been tried in place of the TN display system. One such system uses a strongly dielectric liquid crystal material (N. A. Clarks et al.; Applied Phys. Lett. 36, 899 (1980)). This system, which uses a strongly dielectric chiral smectic phase, and, in particular, a chiral smectic C phase, is attracting considerable interest as a high speed optical switching device. This type of highly dielectric liquid crystal material is already well known, for example, as disclosed in Japanese Laid-Open Patent Application 64-70455, but does not adequately provide the desired characteristics.

SUMMARY OF THE INVENTION

Accordingly, a first object of the present invention is to provide an optically active stilbene compound which adequately demonstrates the characteristics, such as high response, and chemical stability, desired in a liquid crystal material suitable for an optical switching system.

A second object of the present invention is to provide an intermediate to be used in the production of the optically active stilbene compound.

A third object of the present invention is to provide a method of producing the optically active stilbene compound.

A fourth object of the present invention is to provide a liquid crystal composition containing the optically active stilbene compound.

The first object of the present invention is achieved by an optically active stilbene compound as represented by the following formula (I)

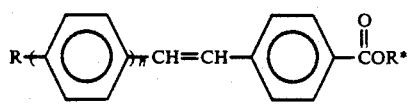

wherein R is an alkoxy group with 20 or less carbon atoms; n is an integer of 1 or 2; and R* is a optically active group.

The second object of the present invention is achieved by a substituted benzylphosphonate compound with the following formula (II):

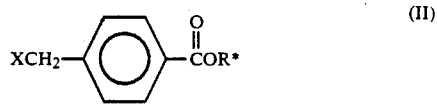

wherein X represents

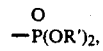

R* is an optically active group with 20 or less carbon atoms, R' is an alkyl group having 1 to 5 carbon atoms, such as a methyl group, an ethyl group, and a butyl group, or an unsubstituted or substituted aryl group.

The third object of the present invention is achieved by a method of producing the optically active stilbene compound of the previously mentioned formula (I) by the reaction of the above-mentioned substituted benzylphosphonate of formula (II) and an aldehyde as represented by the following formula (III):

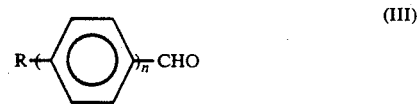

wherein R is an alkoxy group with 20 or less carbon atoms; and n is an integer of 1 or 2.

The fourth object of the present invention is achieved by a liquid crystal composition containing the optically active stilbene compound as represented by the above-mentioned formula (I).

DETAILED DESCRIPTION OF THE PREFERRED EMBODIMENTS

Figure 1:
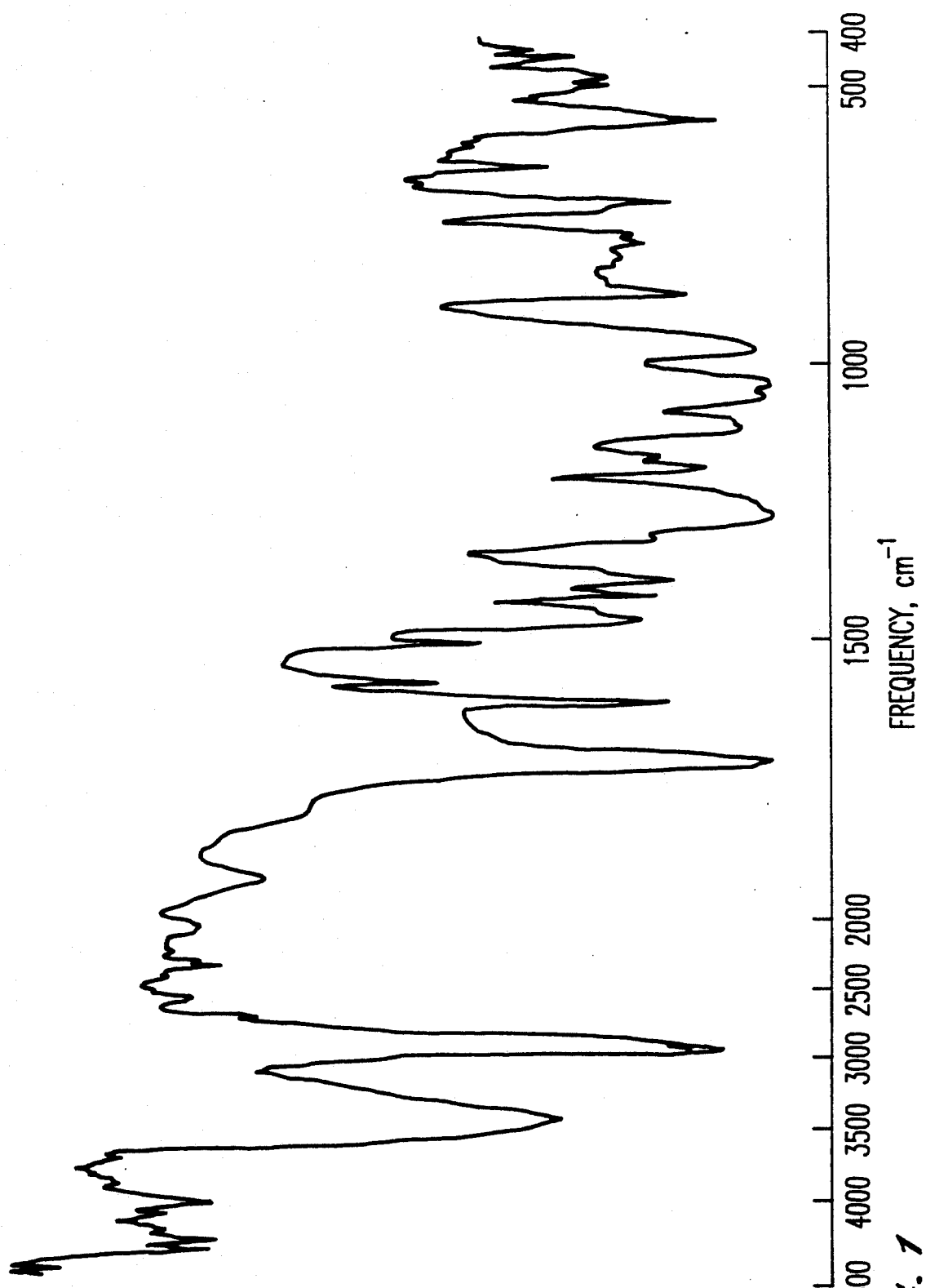
FIG. 1 to FIG. 3 are IR spectra of the stilbene compounds according to the present invention.

The stilbene compound of the present invention represented by formula (I) exhibits characteristics which are extremely useful as a liquid crystal material which must have a high response speed, superior orientation, and the like, as well as photochromic characteristics. It can therefore be used as a reversible optical memory. Specifically, this reversibility can be controlled by light, either over the entire surface or at an optional portion, because the structure of the material changes reversibly from the transform to the cis form where the cis form exhibits no liquid crystal characteristics at a certain specific wavelength $\lambda_1$, and from the cis form to the transform where the transform exhibits liquid crystal characteristics at another wavelength $\lambda_2$.

The compounds represented by formula (I) are generally obtained by the reaction of a substituted benzylphosphonate compound, represented by formula (II), with an aldehyde, represented by formula (III), using a metal alkoxide such as sodium methoxide, sodium ethoxide or potassium t-butoxide, or a base such as sodium hydride, as a catalyst, at a temperature in the room temperature to 100° C. range. Solvents used are ether-type solvents such as diethylether, tetrahydrofuran, dimethoxyethane, and the like, alcohols such as methanol, ethanol, and the like, or amides such as dimethylsulfoxide and the like.

The compound represented by formula (II) may be reacted with the compound represented by formula (III) in a stoichiometric mole ratio.

The compound represented by formula (II) can be obtained, for example, in accordance with the following reaction scheme: First, 4-methylbenzoic chloride of formula (IV) and an optically active alcohol of formula (V) ar reacted in the presence of a base such as pyridine to obtain an optically active 4-methylbenzoic ester of formula (VI). Next, the optically active 4-methylbenzoic ester of formula (VI) is converted to optically active 4-alkoxycarbonylbenzyl bromide (VII) with N-bromosuccinimide, using a conventional method described, for example, in Org. Synth., IV 921 (1963). The compound represented by formula (II) can then be obtained from the optically active 4-alkoxycarbonylbenzyl bromide (VII) and a tri-substituted phosphorous acid by means of a conventional method described, for example, in Chem. Rev., 74, 87 (1972).

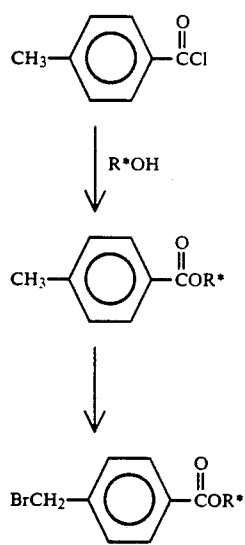

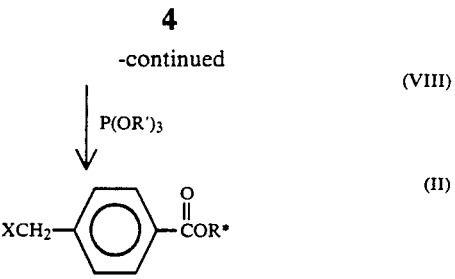

The optically active stilbene compound of the present invention represented by formula (I) exhibits superior performance as a highly dielectric liquid crystal material. It has a high response speed, shows extremely good orientation, and is chemically stable.

The optically active stilbene compound of the present invention represented by formula (I) can be used independently as a highly dielectric liquid crystal material, but it is possible to obtain a composition with improved performance by mixing this stilbene compound with non-chiral smectic liquid crystals or with another highly dielectric liquid crystal material.

The addition of the optically active stilbene compound represented by formula (I) to nematic liquid crystals is effective in preventing the occurrence of a reverse domain in the TN-type cells. In such a case, the optically active stilbene compound of formula (I) is preferably used to the extent of .0.01 to 50 wt % of the resulting composition.

In addition, by adding the optically active stilbene compound of formula (I) to nematic liquid crystals or to chiral nematic liquid crystals, the chiral nematic liquid crystals can be used as a liquid crystal composition in a phase-transition type or in a guest-host type liquid crystal element. In this case, the optically active stilbene compound of formula (I) is preferably used to the extent of 0.01 to 80 wt % of the resulting composition.

The liquid crystal composition containing the compound of the present invention can be used for purposes other than display. It is suitable for us in the field of optoelectronics in various optoelectronic devices such as optoelectronic shutters, optoelectronic diaphragms, optical modulators, optical communication path switches, memories, adjustable-focal-length lenses, and the like.

Among other liquid crystal compounds which can be used jointly with the compound of the present invention, Table 1 gives examples of those which exhibit a highly dielectric chiral smectic phase.

TABLE 1

| No. | Chemical Formula | Phase Transition Temperature (°C.) |
|---|---|---|
| 1 | $C_{10}H_{21}O-\bigcirc-CH=N-\bigcirc-CH=CH-COOCH_2\overset{*}{C}HC_2H_5$ (with $CH_3$ on chiral carbon)<br>p-decyloxybenzylidene-p'-amino-2-methylcinnamate | Crystal $\xrightleftharpoons[]{76°C.}$ SmC* $\xrightleftharpoons[]{95°C.}$ SmA $\xrightleftharpoons[]{117°C.}$ Iso; SmH* (63°C.) |
| 2 | $C_6H_{13}O-\bigcirc-CH=N-\bigcirc-CH=CH-COOCH_2\overset{*}{C}HCH_3$ (with Cl on chiral carbon)<br>p-hexyloxybenzylidene-p'-amino-2-chloropropylcinnamate | Crystal $\xrightleftharpoons[]{60°C.}$ SmH* $\xrightleftharpoons[]{64°C.}$ SmC* $\xrightleftharpoons[]{78°C.}$ SmA $\xrightarrow{}$ Iso |
| 3 | $C_{10}H_{21}O-\bigcirc-CH=N-\bigcirc-CH=C-COOCH_2\overset{*}{C}HC_2H_5$ (with CN on α carbon, $CH_3$ on chiral carbon)<br>p-decyloxybenzylidene-p'-amino-2-amino-2-methylbutyl-α-cinnamate | Crystal $\xrightleftharpoons[]{95°C.}$ SmA $\xrightleftharpoons[]{104°C.}$ Iso; SmH* (70°C., 63°C.) |
| 4 | $C_{12}H_{25}O-\bigcirc-CH=N-\bigcirc-CH=C-COOCH_2\overset{*}{C}HC_2H_5$ (with CN on α carbon, $CH_3$ on chiral carbon)<br>p-tetradecyloxybenzylidene-p'-amino-2-methylbutyl-α-cinnamate | Crystal $\xrightleftharpoons[]{78°C.}$ SmA $\xrightleftharpoons[]{104°C.}$ Iso; SmC* (70°C., 47°C.) |
| 5 | $C_8H_{27}O-\bigcirc-CH=N-\bigcirc-CH=C-COOCH_2\overset{*}{C}HC_2H_5$ (with Cl on α carbon, $CH_3$ on chiral carbon)<br>p-octyloxybenzylidene-p'-amino-2-methylbutyl-α-chlorocinnamate | Crystal $\xrightleftharpoons[]{41°C.}$ SmC* $\xrightleftharpoons[]{66°C.}$ Iso; SmC* (38°C., 27°C.) |
| 6 | $C_8H_{17}O-\bigcirc-CH=N-\bigcirc-CH=C-COOCH_2\overset{*}{C}HC_2H_5$ (with $CH_3$ on α carbon, $CH_3$ on chiral carbon)<br>p-octloxybenzylidene-p'-amino-2-methylbutyl-α-chlorocinnamate | Crystal $\xrightleftharpoons[]{49°C.}$ SmC* $\xrightleftharpoons[]{58°C.}$ SmA $\xrightleftharpoons[]{94°C.}$ Iso |

TABLE 1-continued

| No. | Chemical Formula | Phase Transition Temperature (°C.) |
|---|---|---|
| 7 | $C_8H_{17}O$—⟨phenyl⟩—CH=N—⟨phenyl⟩—OCOCH(CH$_3$)CH$_2$CH$_3$ (*)<br>p-octyloxybenzylidene-p'-amino-2-methylbutylbenzoate | Crystal ⇌ 41°C. SmC* ⇌ 66°C. SmA* ⇌ Iso; 39°C. → SmC* |
| 8 | $C_2H_5$CH(CH$_3$)CH$_2$OCO—CH=CH—⟨phenyl⟩—N=N(O)—⟨phenyl⟩—CH=CH—COOCH$_2$CH(CH$_3$)C$_2$H$_5$<br>4,4-azoxycinnamic acid-bis(2-methylbutyl)ester | Crystal ⇌ 121°C. SmC* ⇌ 134°C. SmA ⇌ 168°C. Iso |
| 9 | $C_8H_{17}$—⟨phenyl⟩—N=CH—⟨phenyl(OH)⟩—OCH$_2$CH(CH$_3$)C$_2$H$_5$<br>4-O-(2-methyl)-butylresorcilydene-4'-octylaniline | Crystal ⇌ 280°C. SmC* ⇌ 55°C. SmA ⇌ 62°C. Iso |
| 10 | $C_8H_{17}O$—⟨phenyl⟩—⟨phenyl⟩—COOCH(CH$_3$)CH$_2$CH$_3$ (*)<br>(2'-methylbutyl)-4'-octyloxybiphenyl-4-carboxylate | Crystal ⇌ 48.5°C. SmA ⇌ 66.5°C. Iso; 44°C. → SmC* |
| 11 | $C_8H_{17}O$—⟨phenyl⟩—⟨phenyl⟩—COO—⟨phenyl⟩—OCH$_2$CH(CH$_3$)C$_2$H$_5$<br>4-(2'-methylbutyl)phenyl-4'-octyloxybiphenyl-4-carboxylate | Crystal ⇌ 78°C. Sm3 ⇌ 80°C. SmC* ⇌ 128.3°C. SmA ⇌ 171.0°C. Cholesteric Mesophase ⇌ 174.2°C. Iso |
| 12 | $C_2H_5$CH(CH$_3$)CH$_2$O—⟨phenyl⟩—⟨phenyl⟩—COO—⟨phenyl⟩—OC$_6$H$_{13}$<br>4-hexyloxyphenol-4-(2''-methylbutyl)biphenyl-4'-carboxylate | Crystal ⇌ 68.8°C. SmC* ⇌ 80.2°C. Cholesteric Mesophase ⇌ 163.5°C. Iso |
| 13 | $C_2H_5$CH(CH$_3$)CH$_2$O—⟨phenyl⟩—⟨phenyl⟩—COO—⟨phenyl⟩—OC$_8$H$_{17}$<br>4-octyloxyphenyl-4-(2''-methylbutyloxy)biphenyl-4''-carboxylate | Crystal ⇌ 76°C. SmC* ⇌ 86.6°C. Cholesteric Mesophase ⇌ 155.4°C. Iso |

TABLE 1-continued

| No. | Chemical Formula | Phase Transition Temperature (°C.) |
|---|---|---|
| 14 | CH₃—C₂H₅CH(CH₂)₃—⟨phenyl⟩—⟨phenyl⟩—COO—⟨phenyl⟩—C₇H₁₅<br>4-heptylphenyl-4(4''-methylhexylbiphenyl-4''-carboxylate | Crystal $\xrightarrow{91.5°C.}$ SmC* $\xrightarrow{93°C.}$ SmA $\xrightarrow{112°C.}$ Cholesteric Mesophase $\xrightarrow{131°C.}$ Iso |
| 15 | CH₃—C₂H₅CH(CH₂)₃—⟨phenyl⟩—⟨phenyl⟩—COO—⟨phenyl⟩—CH₂CHC₂H₅—CH₃<br>4(2''-methylbutyl)phenyl-4-(4''-methylhexyl)biphenyl-4'-carboxylate | Crystal $\xrightarrow{68.8°C.}$ Cholesteric Mesophase $\xrightarrow{80.2°C.}$ $\xrightarrow{163.5°C.}$ Iso<br>74.3°C. ↓ 81.0°C.<br>SmC* ⇌ SmA |

SmC*: High Dielectric Smetic Phase C
SmA: Smetic Phase A
SmH*: High Dielectric Smetic Phase H
Sm3: Smetic Phase Other features of this invention will become apparent in the course of the following description of the exemplary embodiments which are given for illustration of the invention and are not intended to be limiting thereof. Furthermore, it should be noted that there are slight differences between the measured values and the standard values for the phase transition temperatures of the examples, depending upon the measurement method and the purity of the compounds tested.

EXAMPLE 1

[Preparation of 4-n-octyloxy-4'-[(S)-2-methylbutoxycarbonyl] Stilbene

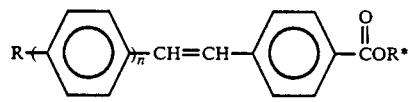

in which R=—OC$_8$H$_{17}$, n=1,

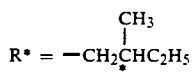

Step A-1. Preparation of 4-methylbenzoic acid [(S)-2-methyl butyl)]ester

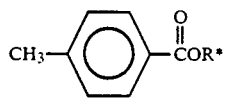

in which

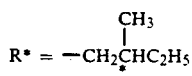

28.51 g (0.23 moles) of a commercially available (S)-2-methylbutanol was dissolved in 100 ml of pyridine. The mixture was cooled and 50 g (0.23 moles) of a commercially available 4-methylbenzoic chloride was added thereto while cooling. The mixture was then allowed to react with stirring at 50° to 60° C. for 2 hours. On completion of the reaction, 300 ml of water and 300 ml of toluene were added, and after vigorous stirring, the toluene layer was separated out and washed with 6N HCl. Washing was continued until this layer was neutral. This toluene layer was dried with anhydrous magnesium sulfate, after which the toluene was distilled away. The residue was further subjected to evaporation under reduced pressure at 118° to 120° C. (5 mm Hg) and the distillate recovered, whereby 59.61 g of the objective 4-methylbenzoic((S)-2-methylbutyl) ester was obtained.

The thus obtained product was subjected to elemental analysis and the result is as follows

|  | Found | Calculated |
|---|---|---|
| % C | 75.73 | 75.69 |
| % H | 8.87 | 8.80 |

Step B-1. Preparation of 4-[(S)-2-methylbutoxycarbonyl]benzylbromide

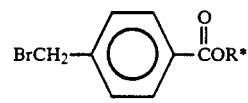

in which

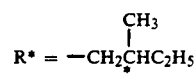

20.63 g (0.1 mole) of the 4-methylbenzoic acid[(S)-2-methylbutyl]ester obtained in Step A-1, 17.80 g (0.1 mole) of N-bromosuccinimide, and 1.32 g (0.005 moles) of benzoyl peroxide were dissolved in 120 ml of dry carbon tetrachloride and allowed to react under reflux for three hours. On completion of the reaction, the reaction mixture was filtered while hot to remove the succinimide, which is a by-product of the reaction, and 27.70 g of a crude form of the objective 4-((S)-2-methyl butoxycarbonyl)benzylbromide was obtained from the filtrate by evaporating off the carbon tetrachloride.

Step C-1. Preparation of 4-[(S)-2-methylbutoxycarbonyl] benzyldiethylphosphate

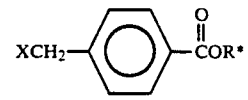

in which

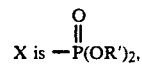

X is —P(OR')$_2$,

R' is —C$_2$H$_5$, and

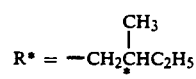

27.70 g of the 4-((S)-2-methylbutoxycarbonyl)benzylbromide obtained in Step B was added dropwise to 33.23 g (0.2 moles) of triethylphosphite and the temperature of the mixture was gradually raised with stirring. The mixture was allowed to react at 140° to 150° C. for 4 hours. On completion of the reaction, the mixture was subjected to evaporation under reduced pressure at 190° to 193° C. (1 mm Hg) and the distillate recovered, whereby 23.67 g of the objective 4-((S)-2-methyl-butoxycarbonyl)benxyldiethylphosphate was obtained.

The thus obtained product was subjected to elemental analysis and the result is a follows:

|  | Found | Calculated |
|---|---|---|
| % C | 59.48 | 59.64 |
| % H | 7.80 | 7.95 |

The chemical structure of this compound was also confirmed by infrared absorption spectrum analysis. The infrared spectrum is shown in FIG. 1.

Figure 2:
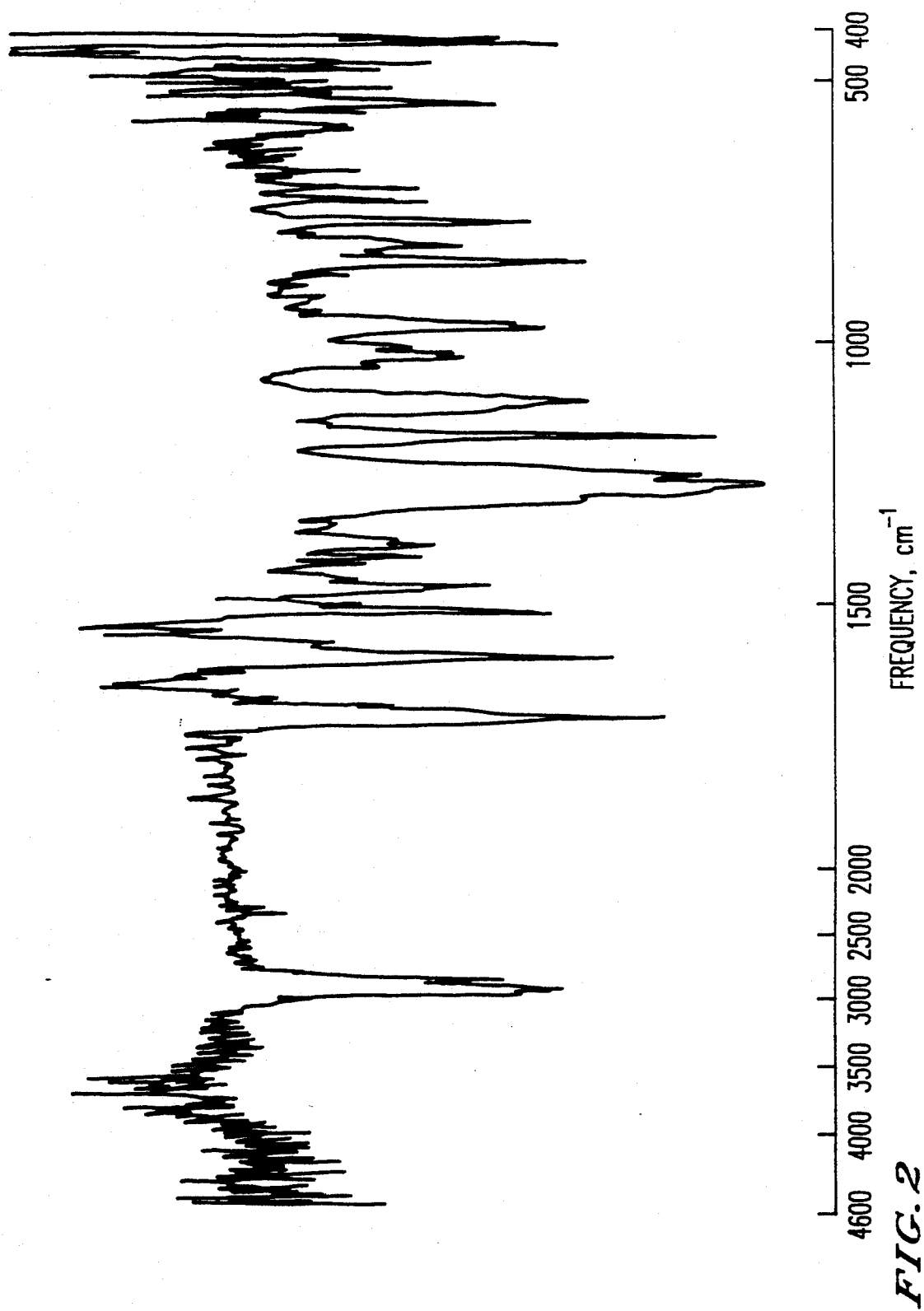

Step D-1. Preparation of 4-n-octyloxy-4'-[(S)-2-methylbutoxycarbonyl)stilbene 3.42 g (0.01 mole) of the 4-[(S)-2-methylbutoxycarbonyl]benzyldiethylphosphate obtained in Step C. was dissolved in 100 ml of dimethoxyethane, then 0.6 g (0.015 moles) of 60% sodium hydride was added with stirring, after which 2.34 g (0.01 mole) of n-octyloxybenzaldehyde was added dropwise over a five minute period. The mixture was then allowed to react at room temperature for 2 hours. On completion of the reaction, 200 ml of water and 200 ml of toluene were added, and after vigorous stirring, the toluene layer was separated out and washed with 6N HCl. Washing was continued until this layer was neutral. This toluene layer was dried with anhydrous magnesium sulfate, after which the toluene was distilled away. A silica gel column chromatography treatment was performed on the residue using toluene as the developing solvent. The crude objective product obtained in this manner was recrystallized three times from ethanol to obtain 2.22 g of the purified product. The optical rotation of this product, $[\alpha]^D$, was found to be $+3.89°$ (chloroform), and the chemical structure of this compound was also confirmed by infrared absorption spectrum analysis. The infrared spectrum is shown in FIG. 2.

EXAMPLES 2 to 7

Liquid crystal compounds of Examples 2 to 7 shown in the following Table 2 were obtained by a similar method to Step D-1 in Example 1, using the aldehydes represented by the general formula (III). The values for the elemental analyses and the phase transition temperatures for the liquid crystal compounds of Examples 2 to 7 obtained in the above manner are also given in Table 2.

TABLE 2

$$R\left(-\bigcirc-\right)_n CH=CH-\bigcirc-\overset{O}{\underset{\|}{C}}-OCH_2\overset{*}{\underset{|}{C}}HC_2H_5$$
$$\phantom{R\left(-\bigcirc-\right)_n CH=CH-\bigcirc-\overset{O}{\underset{\|}{C}}-OCH_2}\overset{CH_3}{\phantom{C}}$$

| Example | R | n | Elemental Analysis | | Phase Transition Temperature (°C.) |
| --- | --- | --- | --- | --- | --- |
| | | | Found (%) | Calculated (%) | |
| 1 | n-C$_8$H$_{17}$O— | 1 | C 79.54<br>H 9.12 | 79.58<br>9.06 | Cryst. ⇌(77.3/68.8) Sc* ⇌(90.1/89.6) S$_A$ ⇌(108.4/107.7) Iso |
| 2 | n-C$_{12}$H$_{25}$O— | 1 | C 80.21<br>H 9.61 | 80.29<br>9.69 | Cryst. —83.5→ S$_A$ ⇌(104.6/103.7) Iso; 71.0 / 82.2 Sc* |
| 3 | n-C$_{10}$H$_{21}$O— | 1 | C 79.97<br>H 9.50 | 79.96<br>9.39 | Cryst. —85.9→ S$_A$ ⇌(105.6/104.5) Iso; 77.4 / 86.2 Sc* |
| 4 | n-C$_9$H$_{19}$O— | 1 | C 79.69<br>H 9.30 | 79.77<br>9.23 | Cryst. —87.1→ S$_A$ ⇌(106.7/105.6) Iso; 74.8 / 89.0 Sc* |
| 5 | n-C$_7$H$_{15}$O— | 1 | C 79.37<br>H 9.02 | 79.37<br>8.88 | Cryst. ⇌(80.3/72.5) Sc* ⇌(91.1/90.5) S$_A$ ⇌(108.0/107.1) Iso |
| 6 | n-C$_6$H$_{13}$O— | 1 | C 79.11<br>H 8.78 | 79.15<br>8.69 | Cryst. —86.4→ S$_A$ ⇌(110.8/110.0) Iso; 82.1 / 87.4 Sc* |
| 7 | n-C$_{18}$H$_{21}$O— | 2 | C 82.01<br>H 9.01 | 82.09<br>8.80 | Cryst. ⇌(168.2/164.9) Sc* ⇌(207.9/196.1) S$_A$ ⇌(237.4/231.5) Iso |

Cryst. denotes crystalline state; Iso, isotropic liquid; S$_A$, smectic phase A; Sc*, chiral smectic phase C.

EXAMPLE 8

[Preparation of 4-n-octyloxy-4'-[(R)-2-methylheptyloxycarbonyl]stilbene

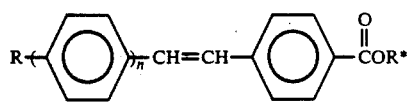

in which R=—OC$_8$H$_{17}$, n=1,

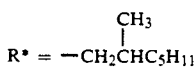

Step A-2. Preparation of 4-methylbenzoic acid [(R)-1-methylheptyl] ester

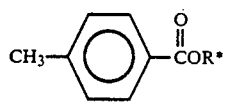

in which

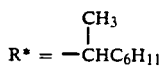

40 g (0.31 moles) of a commercially available (R)-2-octanol was dissolved in 100 ml of pyridine. The mixture was cooled and 47.93 g (0.31 moles) of a commercially available 4-methylbenzoic chloride was added thereto while cooling. The mixture was then allowed to react with stirring at 50° to 60° C. for 2 hours. On completion of the reaction, 300 ml of water and 300 ml of toluene were added, and after vigorous stirring, the toluene layer was separated out and washed with 6N HCl. Washing was continued until this layer was neutral. This toluene layer was dried with anhydrous magnesium sulfate, after which the toluene was distilled away. The residue was further subjected to evaporation under reduced pressure at 144° to 146° C. (2 mm Hg) and the distillate recovered, whereby 70.37 g of the objective 4-methylbenzoic acid [(R)-2-methylheptyl]-ester was obtained.

The thus obtained product was subjected to elemental analysis and the result is as follows:

|      | Found | Calculated |
|------|-------|------------|
| % C  | 77.42 | 77.38      |
| % H  | 9.65  | 9.74       |

Step B-2. Preparation of 4-[(R)-1-methylheptyloxycarbonyl] benzylbromide

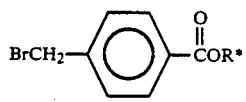

in which

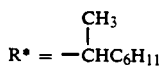

24.84 g (0.1 mole) of the 4-methylbenzoic acid [R)-1-methylheptyl]ester obtained in Step A-2, 17.80 g (0.1 mole) of N-bromosuccinimide, and 1.32 g (0.005 moles) of benzoyl peroxide were dissolved in 120 ml of dry carbon tetrachloride and allowed to react under reflux for three hours. On completion of the reaction, the solution was filtered while hot to remove the succinimide, which is a by-product of the reaction, and 31.40 g of a crude form of the objective 4-[(R)-1-methylheptyloxycarbonyl]benzyl bromide was obtained from the filtrate by evaporating off the carbon tetrachloride.

Step C-2. Preparation of 4-[(R)-1-methylheptyloxycarbonyl] benzyldiethylphosphate

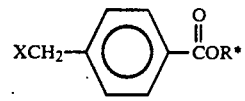

in which

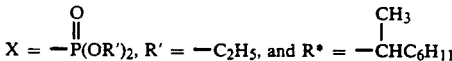

31.40 g of the 4-[(R)-1-methylheptyloxycarbonyl) benzylbromide obtained in Step B-2 was added dropwise to 3.23 g (0.2 moles) of triethylphosphite and the temperature of the mixture was gradually raised with stirring. The mixture was allowed to react at 140° to 150° C. for 4 hours. On completion of the reaction, the excess triethylphosphite was removed by distillation under reduced pressure, whereby 35.12 g of a crude form of the objective 4-[(R)-1-methylheptyloxycarbonyl]benzyldiethylphosphate was obtained.

Figure 3:
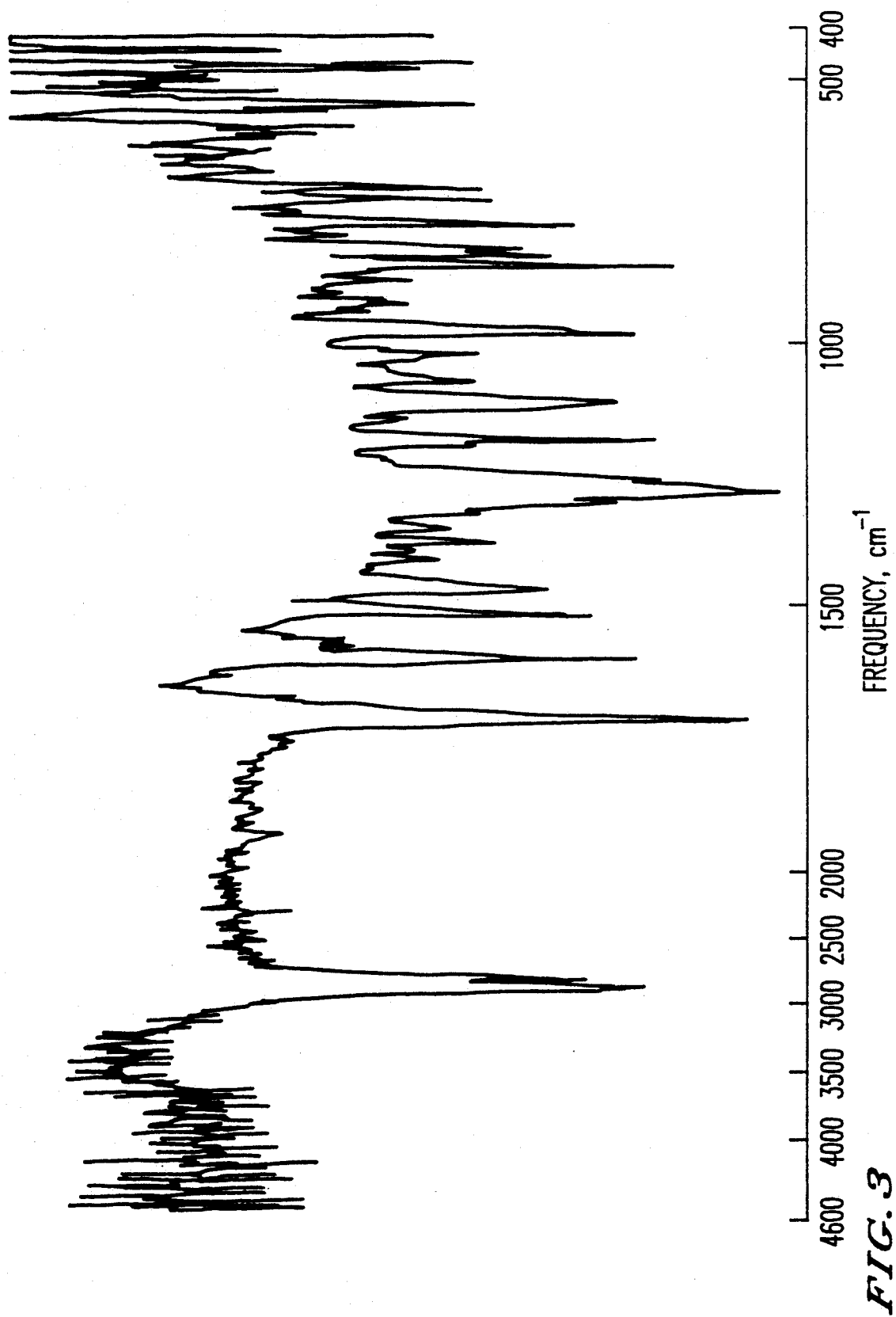

Step D-2. Preparation of 4-n-octyloxy-4'-[(R)-2-methylheptyloxycarbonyl)stilbene 3.84 g (0.01 mole) of the 4-((R)-1-methylheptyloxy carbonyl)benzyldiethylphosphate obtained in Step C-2 was dissolved in 100 ml of dimethoxyethane, then 0.6 g 0.015 moles) of 60% sodium hydride was added with stirring, after which 2.34 g (0.01 mole) of n-octyloxybenzaldehyde was added dropwise over a five minute period. The mixture was then allowed to react at room temperature for 2 hours. On completion of the reaction, 200 ml of water and 200 ml of toluene were added, and after vigorous stirring, the toluene layer was separated out and washed with 6N HCl. Washing was continued until this layer was neutral. This toluene layer was dried with anhydrous magnesium sulfate, after which the toluene was distilled away. A silica gel column chromatography treatment was performed on the residue using toluene as the developing solvent The crude objective product obtained in this manner was recrystallized three times from ethanol to obtain 2.09 g of the purified product. The optical rotation of this product, $[\alpha]^D$, was found to be −41.56° (chloroform). The chemical structure of this compound was also confirmed by infrared absorption spectrum analysis. The infrared spectrum is shown in FIG. 3.

EXAMPLES 9 TO 15

Liquid crystal compounds of Examples 9 to 15 shown in the following Table 3 were obtained by a similar method to the method in Step D-2 in Example 8, using the aldehydes represented by the general formula (III). The values for the element analyses and the phase transition temperatures for the liquid crystal compounds of Examples 9 to 15 obtained in the above manner are also given in Table 3.

TABLE 3

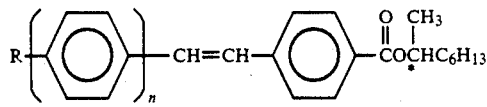

| Example | R | n | Elemental Analysis | | Phase Transition Temperature (°C.) |
|---|---|---|---|---|---|
| | | | Found (%) | Calculated (%) | |
| 8 | n-C$_8$H$_{17}$O— | 1 | C 80.09<br>H 9.65 | 88.13<br>9.54 | Cryst. $\underset{100.6}{\overset{110.0}{\rightleftarrows}}$ Iso |
| 9 | n-C$_{12}$H$_{25}$O— | 1 | C 80.58<br>H 10.19 | 80.72<br>10.07 | Cryst. $\underset{96.7}{\overset{105.1}{\rightleftarrows}}$ Iso |
| 10 | n-C$_{10}$H$_{21}$O— | 1 | C 80.33<br>H 9.92 | 80.44<br>9.82 | Cryst. $\underset{101.3}{\overset{108.7}{\rightleftarrows}}$ Iso |
| 11 | n-C$_9$H$_{19}$O— | 1 | C 80.21<br>H 9.83 | 80.29<br>9.69 | Cryst. $\underset{101.1}{\overset{111.9}{\rightleftarrows}}$ Iso |
| 12 | n-C$_7$H$_{19}$O— | 1 | C 79.83<br>H 9.56 | 79.96<br>9.39 | Cryst. $\underset{97.2}{\overset{108.5}{\rightleftarrows}}$ Iso |
| 13 | n-C$_6$H$_{13}$O— | 1 | C 79.63<br>H 9.35 | 79.77<br>9.23 | Cryst. $\underset{93.6}{\overset{104.4}{\rightleftarrows}}$ Iso |
| 14 | n-C$_{10}$H$_{21}$O— | 2 | C 82.12<br>H 9.30 | 82.35<br>9.22 | Cryst. $\underset{93.6}{\overset{104.4}{\rightleftarrows}}$ Sc* $\underset{179.2}{\overset{180.0}{\rightleftarrows}}$ S$_A$ $\underset{182.1}{\overset{182.9}{\rightleftarrows}}$ Iso |
| 15 | n-C$_8$H$_{17}$O— | 2 | C 82.10<br>H 8.98 | 82.18<br>8.95 | Cryst. $\underset{159.3}{\overset{168.3}{\rightleftarrows}}$ Sc* $\underset{180.8}{\overset{184.4}{\rightleftarrows}}$ S$_A$ $\underset{196.9}{\overset{198.2}{\rightleftarrows}}$ Iso |

Cryst. denotes crystalline state; Iso, isotropic liquid; S$_A$, smectic phase A; Sc*, chiral smectic phase C.

APPLICATION EXAMPLE 1

The surfaces of a pair of transparent electrode sheets were coated with polyvinyl alcohol (PVA), after which the surfaces were rubbed for a parallel orientation treatment.

Test cells were prepared by positioning the two sheets in opposition with a space of 3 μm between them, with a PVA film on the inside. The optically active stilbene compound of Example 1 was then poured into the cell formed in this manner, after which the cell was placed between two sheets of polarizers in a cross-polarized orientation to obtain a liquid crystal display element. When a potential of 30 volts was applied between the electrodes, a good, clear contrast was obtained and a switching action with a high response speed (about 150 μsec) was observed.

APPLICATION EXAMPLE 2

A liquid crystal composition A was prepared by mixing the following components with the following formulation:

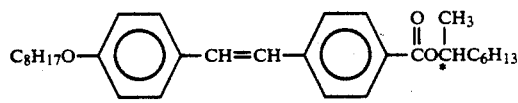

12.0 wt. %
(Stilbene Compound Obtained in Example 8)

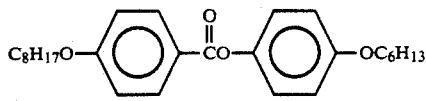

35.3 wt. %

-continued

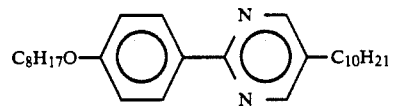

52.7 wt. %

The phase transition temperatures (° C.) of this composition were as follows.

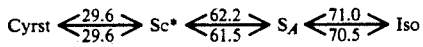

A pair of glass plates, on which an ITO film was formed as a transparent electrode, were coated with Polyimide JIB-1 (manufactured by Japan Synthetic Rubber Co., Ltd.). The surfaces were rubbed for a parallel orientation, and test cells were prepared by positioning the glass substrates in opposition, separated by a space of 2 μm, with the polyimide film on the inside, then joining the glass plates using an adhesive sealing agent (Trademark "Lixon Bond" manufactured by Chisso Corporation).

This cell was then filled with the previously prepared liquid crystal composition A in a uniform liquid state in the isotropic phase, after which the filled cell was placed between two sheets of polarizer in a cross-polarized orientation to obtain a liquid crystal display element. At room temperature, when a potential of 20 volts was applied between the electrodes, a good, clear contrast was obtained and a switching action with a high response speed (about 250 μsec) was observed.

The optically active stilbene compound of the present invention represented by general formula (I) exhibits superior characteristics as a highly dielectric liquid crystal material. It has a high response speed, shows extremely good orientation, and is chemically stable.

The optically active stilbene compound of the present invention represented by the general formula (I), when added to nematic liquid crystals, is effective in preventing the occurrence of a reverse domain in TN-type cells.

Accordingly, the liquid crystal composition containing the compound of the present invention of the formula (I) can be used for purposes other than display. It is suitable for use in the field of optoelectronics in various optoelectronic diaphragms devices such as optoelectronic shutters, optoelectronic, optical modulators, optical communication path switches, memories, focal-length-adjustable lenses, and the like.

What is claimed is:

1. An optically active stilbene compound of the formula (I):

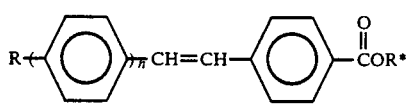  (I)

wherein R is an alkoxy group with 20 or less carbon atoms; n is an integer of 1 or 2; and R* is an optically active group selected from the group consisting of 1-methylheptyl, 2-methylheptyl and 2-methyloctyl.

2. A method of producing an optically active stilbene compound of formula (I) by the steps comprising reacting a substituted benzylphosphonate of formula (II) and an aldehyde of formula (III):

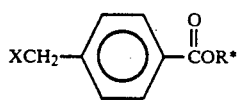  (II)

+

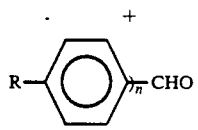  (III)

↓

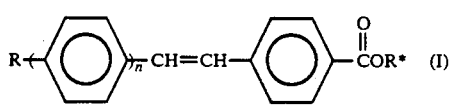  (I)

wherein X is

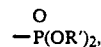

$-P(OR')_2$,

R' is an alkyl group having 1 to 5 carbon atoms, or an unsubstituted or substituted aryl group, R* is an optically active group selected from the group consisting of 1-methylheptyl, 2-methylheptyl and 2-methyloctyl, and n is an integer of 1 or 2.

* * * * *

UNITED STATES PATENT AND TRADEMARK OFFICE
CERTIFICATE OF CORRECTION

PATENT NO. : 5,227,512
DATED : July 13, 1993
INVENTOR(S) : Masayuki Shoshi

It is certified that error appears in the above-indentified patent and that said Letters Patent is hereby corrected as shown below:

Column 3, line 13, "(V) ar reacted" should read --(V) are reacted--.

Column 6, table 1, number 5, "$C_8H_{27}O$" should read --$C_8H_{17}O$--.

Column 8, table 1, number 13, "$OC_9H_{17}$" should read --$OC_8H_{17}$--.

Column 11, line 13, "[(S)-2-methylbutoxycarbonyl] Stilbene" should read --[(S)-2-methylbutoxycarbonyl]stilbene]--.

Column 13-14, table 2, number 7, "n-$C_{18}H_{21}O$-" should read --n-$C_{10}H_{21}O$--.

Column 14, line 61, "tyloxycarbonyl]stilbene" should read --tyloxycyarbonyl]stilbene]--.

Column 16, line 20, "[(R)-1-methylheptyloxycarbonyl)" should read --[(R)-1-methylheptyloxycarbonyl]--;
line 32, "[(R)-2-methylheptyloxycarbonyl)" should read --[(R)-1-methylheptyloxycarbonyl]--.

UNITED STATES PATENT AND TRADEMARK OFFICE
CERTIFICATE OF CORRECTION

PATENT NO. : 5,227,512
DATED : July 13, 1993
INVENTOR(S) : Masayuki Shoshi

It is certified that error appears in the above-indentified patent and that said Letters Patent is hereby corrected as shown below:

```
Column 19, line 14, "optoelectronic diaphragms devices"
should read --optoelectronic devices--;
            line 15, "optoelectronic, optical" should read
--optoelectronic diaphragms, optical--.
```

Signed and Sealed this

Eighteenth Day of October, 1994

Attest:

BRUCE LEHMAN

Attesting Officer

Commissioner of Patents and Trademarks